United States Patent [19]
Neukermans et al.

[11] 3,990,797
[45] Nov. 9, 1976

[54] DIFFRACTION MONITORING OF RAYLEIGH MODE JETS

[75] Inventors: Armand P. Neukermans, Palo Alto, Calif.; Dale R. Ims, Rochester, N.Y.

[73] Assignee: Xerox Corporation, Stamford, Conn.

[22] Filed: May 27, 1975

[21] Appl. No.: 581,393

[52] U.S. Cl. ............................. 356/111; 356/102
[51] Int. Cl.² ........................................ G01B 9/02
[58] Field of Search ........ 356/111, 102, 208, 106 R, 356/109; 250/574

[56] References Cited
UNITED STATES PATENTS
3,834,818   9/1974   Meric ................................. 356/102

OTHER PUBLICATIONS
Cornillaut; "Particle Size Analyzer;" Applied Optics, vol. 11, No. 2, 265 2/72.

*Primary Examiner*—John K. Corbin
*Assistant Examiner*—Conrad Clark
*Attorney, Agent, or Firm*—James J. Ralabate; Michael H. Shanahan; George J. Cannon

[57] ABSTRACT

A light diffraction technique is set forth for monitoring the behavior of small liquid jets operating in the Rayleigh mode. This monitoring enables measurement of jet parameters, and thereby further enables on-line control of these parameters.

6 Claims, 8 Drawing Figures

DIFFRACTION MONITORING OF RAYLEIGH MODE JETS

BACKGROUND OF THE INVENTION

Particles of uniform size and shape have uses in numerous chemical and mechanical applications, especially when the shape is spherical. For example, toner particles for use in xerographic development systems should, for maximum efficiency, be as near spherical as possible and display a very small size variance pattern. Toner exhibiting such characteristics is also extremely useful in the testing and analysis of xerographic-type sub-systems which act with or upon particulate materials.

Lord Rayleigh first demonstrated that liquid jets exhibits a natural instability and break into segments of random length. He showed further that when a periodic pressure disturbance is coupled to a small liquid jet there occurs, over a certain frequency interval, a growth of the perturbation which ultimately causes the jet to break up into uniform segments. These segments are reshaped by surface tension into uniformly sized spheres. Optimum segment lengths or wavelength ($\lambda$) was found to be related to the radius of the jet (a) by $\lambda = 9a$. At this wavelength the disturbance has a maximum growth rate. Controlled breakup is possible, in principle, for all wavelengths larger than the circumference of the jets ($\lambda > 2 \pi a$), but experimentally it has been found that the condition $7a < \lambda < 36a$ must be satisfied in order to produce coherent breakup. See, for example, J. M. Schneider, N. R. Lindblad, C. D. Hendricks, Jr., and J. M. Crowley, *Journal of Applied Physics*, 38, 2599 (1967).

Broadly, the Rayleigh mode droplet formation technique can be seen in FIG. 1. A solution 3, consisting of the material to be sprayed, dissolved in a suitable solvent if necessary and dyed or pigment loaded as desired, is sealed under pressure in vessel 1. An opening in the vessel is covered by an aperture plate 4 which contains an array of holes. Within the enclosure of vessel 1, and at least partially submerged in solution 3, is the radiating face of an ultrasonic transducer 2.

A liquid jet of velocity $V_j$ is formed at each of the apertures by the hydrostatic pressure in the vessel 1. The acoustic signal from the transducer 2 modulates the pressure at the apertures and causes a perturbation in the jet. If the wavelength ($\lambda$) of the perturbation is within the limits $7a-36a$, the perturbation will grow and cause the jet to break up coherently.

Each volume ($\pi a^2 \lambda$) of the jet is then converted by surface tension into a droplet of volume ($4 \pi R^3/3$), where R is the droplet radius. Since coherent breakup is possible over a wide range of wavelengths, without varying any other parameters the volume of the droplets obtained can be controlled by modifying the frequency $f$ of the acoustic perturbation, since $\lambda = V_j/f$.

After the solvent contained in the droplet is removed by evaporation under the appropriate conditions, a virtually perfect solid, spherical particle remains. The size of the sphere thus produced depends not only on the size of the original liquid sphere, but also on the various concentration of the materials in the sprayed liquid.

Final particle size may therefore be controlled by either acoustical drive frequency, jet velocity (vessel pressure), material concentrations and/or aperture size. Of these controlling variables, aperture size by far provides the greatest control range; final particle size will, in general, be on the order of the size of the aperture.

After breakup of the liquid jet, an array of equal sized droplets is formed. When an array of apertures is used, the droplets will vary in size somewhat from jet to jet due to aperture size variation. However, apertures such as those existing in electro-deposited nickel screens have a small size variation (for example, those available from Buckbee-Mears Co., St. Paul, Minn.). Therefore, at the time of droplet formation, the droplet size distribution is quite small.

The regularity of the droplet array is eroded by air drag on the particles; this may result in a collision between two or more particles, which in turn will cause these droplets to coalesce into new droplets with two, three, or more times the volume of the original droplets. The coalesced droplets with their increased size result in a reduction in the overall particle size uniformity.

Stroboscopic light sources and microscopes have been used in the past to observe this breakup; however, when the jet radius becomes very small (on the order of $5\mu m$) these observations become rather difficult. The minimum fluid velocity necessary to form a jet increases as $a^{-1/2}$, and therefore if it is desired to meet the condition $\lambda = 9a$, the frequency ($f = V_j/\lambda$) increases, not only as $a$ decreases, but also because the minimum workable jet velocity increases. Typically, for a $5\mu m$ radius jet working at 10 meters/second, the optimum frequency is 220 KHz. Most conventional stroboscopes have a maximum operating frequency of 2500 Hz, so that it is necessary to synchronize the stroboscope on a large subharmonic of the drive frequency. This limitation and the image smearing caused by the high particle velocity, small particle size, and finite light pulse length can make observations quite difficult and confusing. Recent wide bandwidth electro-optic modulators allow stroboscopic observations at much higher frequencies, but they require more complex equipment. Finally, the required microscopic observations are difficult to make. A $5\mu m$ radius jet produces droplets on the order of $9\mu m$ in radius; these small particles are hard to observe with telescopic microscopes because of their low magnification. Conventional microscopes with small working distances are ruled out because the spray tends to coat the objective.

An array of uniformly sized, uniformly spaced droplets such as produced by an assembly of parallel jets operating in the Rayleigh mode produces a well-known light diffraction pattern. However, it should be noted that if the frequency of the acoustic disturbance is tuned beyond the region where coherent breakup is possible, the pattern disappears abruptly. The diffraction technique described herein greatly simplifies measurement of all the important particle and jet parameters. It furthermore provides a measure of overall sprayer performance, i.e., particle size uniformity.

BRIEF SUMMARY OF THE INVENTION

It is therefore an object of this invention to provide the above-described desirable features.

It is another object of this invention to provide a relatively simple method for monitoring the behavior of small liquid jets operating in the Rayleigh mode.

It is a further object of this invention to provide a method to control the breakup conditions of small liquid jets operating in the Rayleigh mode.

It is a still further object of this invention to provide a method for determining jet malfunctions, e.g., clogging, of small jets operating in the Rayleigh mode.

It is an even still further object of this invention to provide a method for selection of the optimum operating conditions of small liquid jets operating in the Rayleigh mode.

These and other objects are accomplished by providing a light diffraction technique for monitoring the behavior of small liquid jets operating in the Rayleigh mode. This monitoring enables measure of jet parameters and thereby further enables on-line control of these parameters.

BRIEF DESCRIPTION OF THE DRAWINGS

For a better understanding of the invention as well as other objects and further features thereof, reference is made to the following detailed disclosure of the invention taken in conjunction with the accompanying drawings wherein.

DESCRIPTION OF THE PREFERRED EMBODIMENTS

Figure 1:
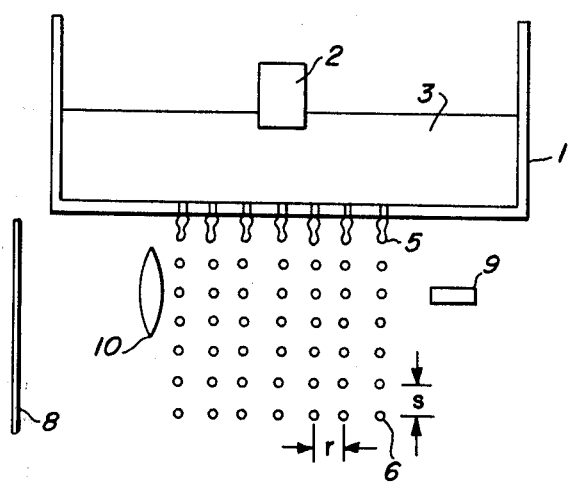
FIG. 1 is a partially schematic, cross-sectional view of a spraying apparatus suitable for use with the instant invention.

Referring again to FIG. 1, the general arrangement of elements, as partially described above, for producing the diffraction pattern can be seen. Laser 9 is directed such that its beam travels perpendicularly to the droplet streams, through condensing lens 10 and onto screen 8 where the diffraction pattern is displayed.

The vertical dimension s (the breakup wavelength) is set by the frequency of operation and jet velocity. The horizontal separation r is simply the distance between jets, which is usually taken to be periodic, but with a much longer period than that of the particles within a stream. This vertical periodicity in the pattern, in the order of $2 \times 10^{-5}$ meters, can be used to establish a diffraction pattern; a diffraction pattern which, in turn, may be used to "read" the behavior of the spraying process.

Figure 2:
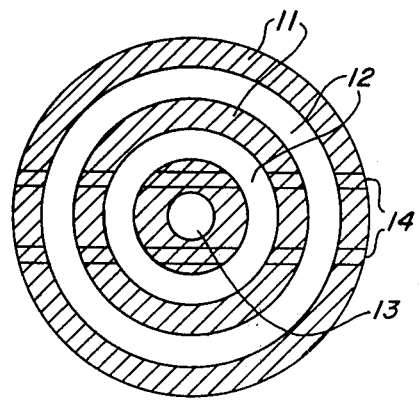
FIG. 2 is a schematic representation of a diffraction pattern showing various characteristics thereof.

Typical diffraction patterns are comprised of an array of dots: dot separation in the x-direction is inversely proportional to the separation between jets; the dot separation in the y-direction is inversely proportional to the droplet separation. Attention is now directed to FIG. 2 which shows an exemplary diffraction pattern of a spraying apparatus operating in the Rayleigh mode. Since the inter-jet spacing r is usually fairly large the dot separation in the x-direction is very small and often appears as a solid line(s) 14. Super-imposed on this rectangular dot matrix there appears a circular pattern comprising concentric bright and dark rings, 11 and 12 respectively, the size of which is inversely related to the diameter of the droplets.

Figure 3:
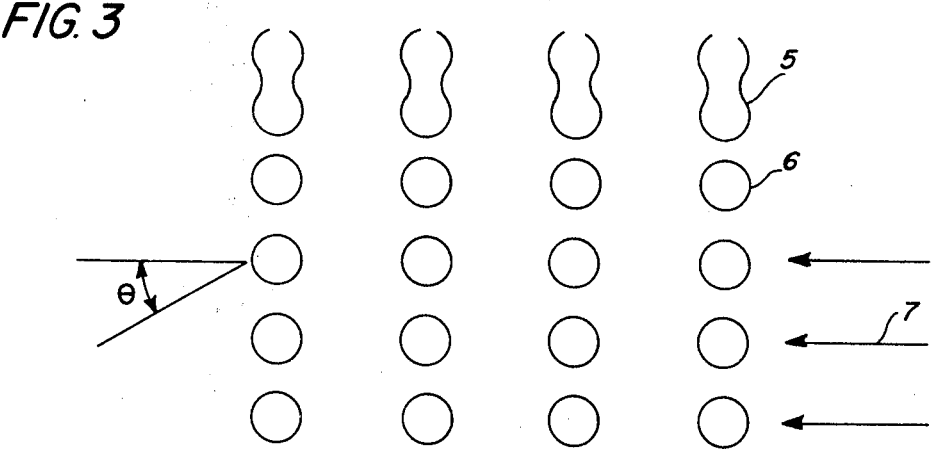
FIG. 3 is a more detailed view of the droplet formation process which occurs in FIG. 1.
Figure 4:
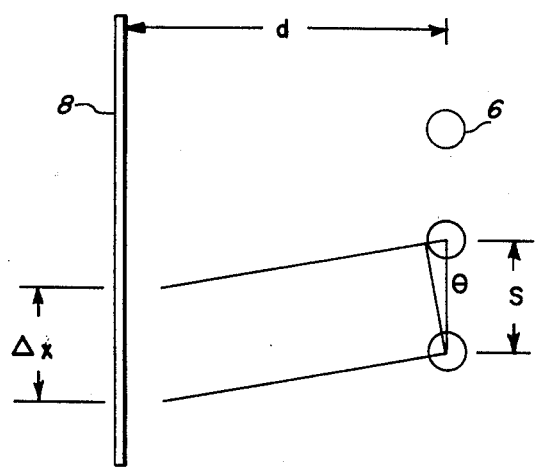
FIG. 4 is an even more detailed schematic view of the droplets from one jet stream.

Directing attention now to FIGS. 2-4 the computations for vertical drop separation and velocity will be described. The vertical periodic pattern produces constructive interference at angles $\tan \theta_n$ $\theta_n = n\lambda_i/s$, where $\lambda_i$ is the wavelength of the incident radiation from the laser, $\theta_n$ is the angle of diffraction at the $n^{th}$ line, and hence the fringe separation $\Delta x$ (i.e., the spacing between horizontal lines 14) on the screen at a distance $d$ is simply $\Delta x = \lambda_i d/s$ (See FIG. 4). In practice, $\Delta x$ and $d$ are measured, $\lambda_i$ is known and s is determined from $s = \lambda_i d/\Delta x$. The jet velocity is $V_j = sf$, where $f$ is the acoustic driving frequency of transducer 2.

For a complete understanding of the technique of particle size determination utilizing a circular diffraction pattern, see H. C. Van De Hulst, *Light Scattering by Small Particles*, J. Wiley, New York, 1962.

For the present situation it is sufficient to describe the procedure as follows. The distance p, shown in FIG. 2, between the center of the diffraction pattern and the center of the second dark ring is measured. Also measured is the distance d between the particles and the screen on which the pattern is projected. Generally, this distance is taken to be that between the condensing lens 10 shown in FIG. 1 and the screen 8, which is also the focal length of the lens. The particle radius a is calculated from the equation:

$$a = \frac{(7.016)}{\sin \theta}$$

Where $\sin \theta = p/d$.

Reduction in particle size uniformity causes a degradation of the diffraction pattern. This degradation is evidenced by a reduction in light intensity contrast between light and dark rings, 11 and 12 respectively in FIG. 2 and a reduction in the number of rings.

Therefore, in its most simple form, the instant invention provides for the visual interpretation of operation parameters of a Rayleigh mode spraying apparatus by diffraction pattern analysis. More intense and numerous concentric rings produce a smaller particle size distribution. The distance between any two of the horizontal lines x is inversely related to the wavelength of the jet(s), i.e., the more horizontal lines visible, the more consistent the wavelength throughout the array.

The above technique is very convenient for monitoring the breakup of the jets and clogging of the nozzles, or for measuring the droplet diameter at the instant of formation. In general, it monitors the condition of a Rayleigh sprayer very near the nozzle. However, it is also possible to measure the distribution of the sprayed droplets while drying, their average diameter, their rate of evaporation (from their size), etc. some distance away from the nozzle, the periodicity of the droplet arrangement is destroyed. Hence the horizontal lines as presented in FIG. 2 are absent from the diffraction pattern, but the ring pattern is still present, and it is still true that the more uniform the particle distribution, the more intense and better defined is the diffraction pattern. The average diameter can still immediately be found from the above expression for a, and the relative intensities of the rings allows for the determination of the particle size distribution.

Figure 5:
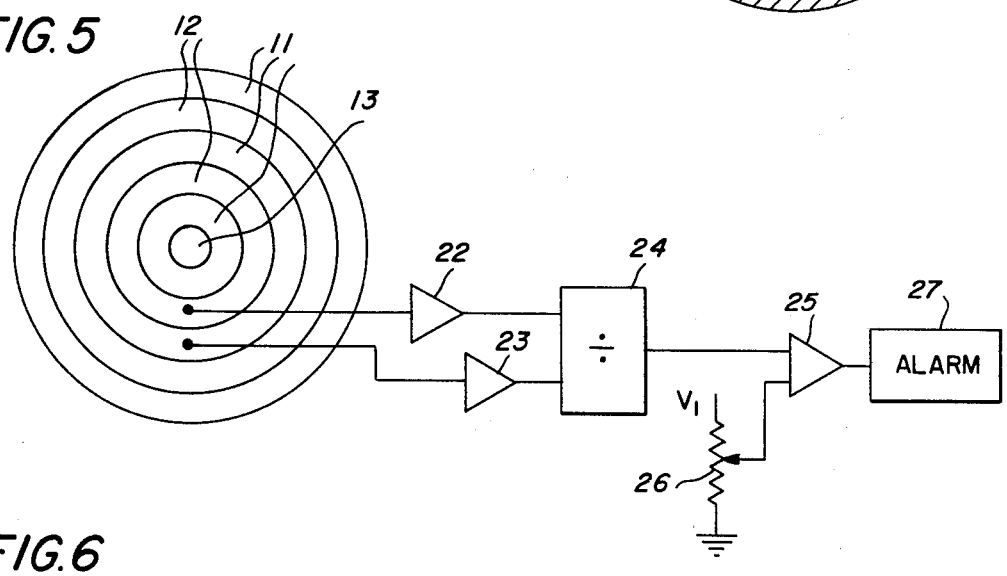
FIG. 5 is a schematic representation of an alarm system for signaling production of particles outside a chosen range of uniformity.
Figure 6:
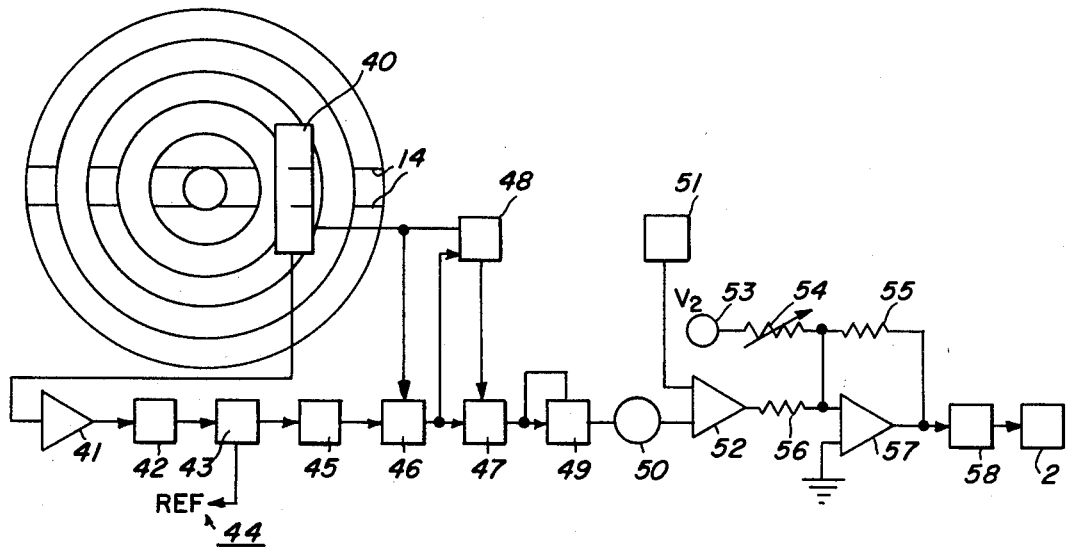
FIG. 6 is a schematic representation of a system for controlling the frequency at which the transducer operates.
Figure 7:
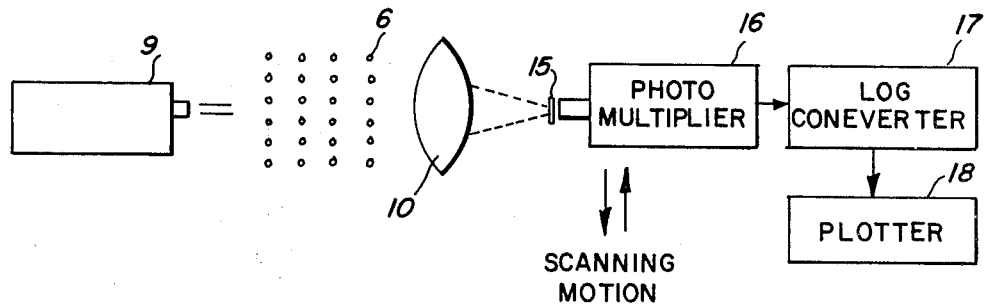
FIG. 7 is a schematic representation of a system for producing a graphic representation of the diffraction pattern.
Figure 8:
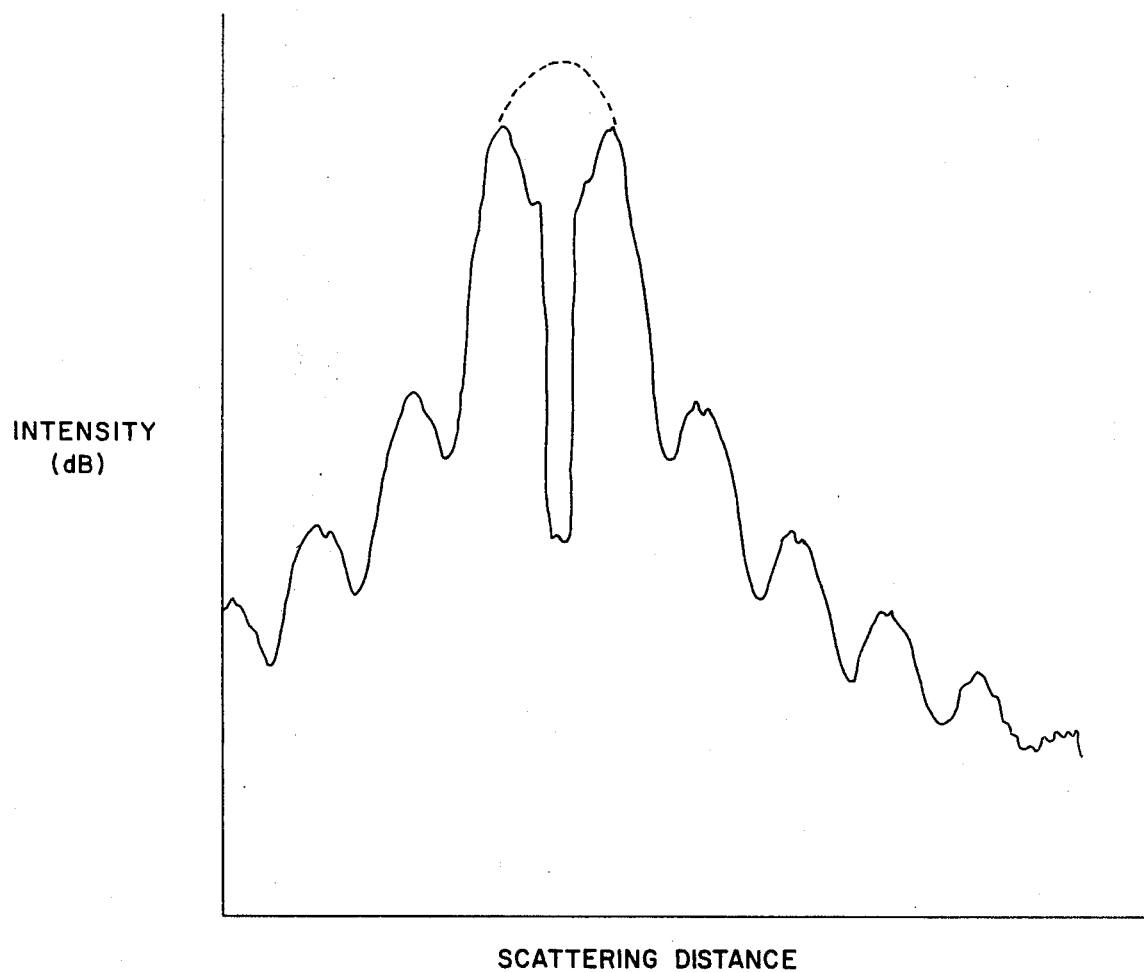
FIG. 8 is an exemplary graphical representation of a diffraction pattern produced by the system of FIG. 7.

FIGS. 5 and 6 show exemplary apparatus for accomplishing automatic or semiautomatic control of the spraying process by electro-mechanical means.

Attention is now directed to FIG. 5 wherein an alarm system for signaling the production of particles outside a chosen range of uniformity, i.e., and unacceptable proportion of coalesced particles, is described. Photodiodes, such as those available from Hewlett Packard, 20 and 21 are placed within adjoining dark and light concentric rings as shown in the drawing. Optimally, because of higher contrast ratios, photodiode 20 is in the first dark ring, and photodiode 21 is in the first bright ring. The outputs of the two photodiodes are amplified by amplifiers 23 and 22 respectively and the signals divided by an analog divider 24, such as available from Function Modules, Inc., Irvin, California. The ratio of the two is fed to a comparator 25 where it is compared to a preset (adjustable) level determined by potentiometer 26. When the ratio decreases below the minimum acceptable preset level, an alarm 27 is triggered.

Potentiometer 26 sets the minimum value for the intensity difference between the maximum and minimum intensities shown, for example, by the first two rings in the pattern of FIG. 5. For purpose of illustration, the chart set forth below indicates ranges (in db.) of differences and the corresponding per cent of singlets of standard size in the spray.

| | |
|---|---|
| .5 – 1.0 db | 68% |
| 1.8 – 2.75 db | 75% |
| 3.2 – 5.0 db | 81% |
| 4.5 – 7.5 db | 85% |
| 6.5 – 9.5 db | 89% |
| 10.0 – 16.0 db | 95% |

This measurement can also be made after all possibility of further coalescence is substantially eliminated, i.e., after the particles are hardened. A convenient measurement technique is to draw the hardened particles in the form of a dilute aerosol through a glass-walled sample chamber through which a laser beam is directed; the diffraction pattern is measured in a screen located in the opposite side of the sample chamber from the laser. An output of 75% is quite satisfactory for most purposes and easily obtainable from spraying apparatus operating in the Rayleigh mode.

FIG. 6 is a schematic representation of an electromechanical apparatus for controlling the frequency *f* at which ultrasonic transducer 2 operates. Linear photodiode array 40, such as described by Melen in Electronics, May 24, 1973, Vol. 46, No. 11, pp. 106–111, e.g., and MOS with an internal clock, samples the light intensity sequentially along a vertical path which crosses at least two of the horizontal lines 14 within the diffraction pattern. The output of this array appears as a pulse train at the internal clock rate. This pulse train is smoothed by low pass filter 42 after amplification at 41. The output of the filter is fed into a comparator 43 which has a reference set, by signal 44, at a level above the signal in the dark areas, but below the signal in the light areas. The comparator therefore detects the bright bands and triggers a monostable one-shot multivibrator 45. The multivibrator drives a flip-flop 46 which changes state at each bright band. The flip-flop is reset at the end of each cycle of the diode array. Logic control circuitry 48 assures that if a measurement pulse is being processed at reset, it will not be passed on. This prevents errors at the beginning and end of the array cycle.

Pulse length voltage converter 47 converts the pulse length (time) to a voltage which appears at the unit's output as a pulse (may be inhibited by the logic). The sample and hold unit 49 is signal triggered; it samples the height of the pulse from the converter and holds it until the next pulse comes along.

A low-pass filter 50 may be needed to remove unwanted noise. The output of the sample and hold unit 49 is fed to a level shifter 52 to get the voltage down to a level of near zero (+ or −). The frequency adjust component, comprised of elements 53, 54, 55, 56 and 57 adds algebraically the frequency set signal and the error signal. The resulting signal is fed to the voltage controlled oscillator 2 to adjust the output frequency.

Although the specific apparatus and process steps have been described, other elements and steps may be used where suitable.

For example, other accurate methods of "reading" the diffraction pattern can be devised. A convenient graphic representation of the particle size distribution can be obtained by scanning the diffraction pattern area with a photomultiplier which is tied sequentially to a log converter and a plotter. Such an arrangement of elements is shown in FIG. 7. As in FIG. 1, the beam from laser 9 (for example, a He-Ne laser, Spectra Physics Model 132) is directed through the array of particles 6. A beam expander and spatial filter may be used therebetween if desired.

The light is condensed by lens 10 and the undifracted portion thereof eliminated by stop 15 which is placed at the focal point.

A photomultiplier 16 (for example, an EMI 9558) with a small aperture (in the order of about 0.1 to about 0.2mm) scans the scattering pattern in the focal plane. The output of the photomultiplier is fed into a logarithmic amplifier 17 (for example, Model 755P available from Analog Devices). This amplifier produces a linear voltage output with accurance better than 1 per cent for negative current input. The output voltage is recorded with plotter 18 which can be, for example, a Moseley 7100B Strip Chart Recorder.

The graphical output of plotter 18 is exemplified in FIG. 8. The Intensity vs. Distance curse provides much the same information as the other methods of pattern interpretation set forth above. The maxima and minima on the graph represent, respectively, the bright and dark rings observable on the pattern. The graph is generally symetrical about the midline, and again, the more maxima present the more nearly the system is operating in the preferred mode. It is not unusual for as many as 15–20 maxima to appear, nor is it unusual to observe as many horizontal lines.

In summary then, the following methods and operations have been described for controlling a spayer operating in the Rayleigh mode:

1. Measurement of velocity and operating point,
2. Determination of optimum range of operation by brightness and sharpness of pattern,
3. Feedback systems to control pressure or frequency or indicate malfunctions (absence of acoustic signal, insufficient amplitude, etc.), and
4. Scan nozzle to determine zones not operating adequately.

It will be understood that various changes in details, materials, steps and arrangements of parts, which have herein been described and illustrated in order to explain the nature of the invention, will occur to and, may be made by those skilled in the art upon a reading of the disclosure within the principle scope of the invention.

What is claimed is:

1. A method for monitoring the behavior of jets producing streams of droplets by operating in the Rayleigh mode, comprising:

a. intercepting in the proximity of said jets said streams of droplets with coherent radiation, $\lambda_1$, said radiation being directed orthogonal to the direction of travel of said stream of droplets, wherein said radiation is diffracted into a pattern of concentric, alternating light and dark rings superimposed upon at least one pair of dark bands; and b. intercepting said pattern upon a screen at a distance, *d*, from said streams; said pattern being characterized by the distance between the dark bands $\Delta X = \lambda_1 d/s$ where *s* is the separation between individual droplets in a stream of droplets and by the distance from the center of the concentric bands to the middle of the second dark ring *p* where the droplet radius $a = 7.016 \div p/d$.

2. The method of claim 1 further including the steps of:

c. intercepting said streams of droplets with said coherent radiation at a location sufficiently remote from the jets to form another diffraction pattern lacking said pair of dark bands;

d. calculating the droplet radius at the remote location; and e. comparing the droplet radius at the remote location to the droplet radius in the proximity of said jets to determine drying rate of said droplets.

3. A method for monitoring separation, *s*, between individual droplets in a stream of droplets produced by a jet operating in the Rayleigh mode, comprising:

a. intercepting in the proximity of said jet said stream of droplets with coherent radiation, $\lambda_1$, said radiation being directed orthogonal to the direction of travel of said stream of droplets, wherein said radiation is diffracted into a pattern of concentric, alternating light and dark rings superimposed upon at least one pair of dark bands;

b. intercepting said pattern upon a screen at a distance, *d*, from said stream wherein the distance between the dark bands of the intercepted pattern $\Delta X = \lambda_1 d/s$; and c. monitoring $\Delta X$ for indication of any change in the value of *s*.

4. The method of claim 3 wherein the separation, *s*, between individual droplets in each of a plurality of streams is monitored by scanning the coherent radiation.

5. A method for determining the velocity, $V_j$, of a stream of droplets produced by a jet operating in the Rayleigh mode at a frequency *f*, comprising:

a. intercepting in the proximity of said jet said stream of droplets with coherent radiation, $\lambda_1$, said radiation being directed orthogonal to the direction of travel of said stream of droplets, wherein said radiation is diffracted into a pattern of concentric, alternating light and dark rings superimposed upon at least one pair of dark bands;

b. intercepting said pattern upon a screen at a distance *d*, from said stream wherein the distance between the dark bands of the intercepted pattern, $\Delta X = \lambda_1 d/s$, where *s* is the separation distance between individual droplets in said stream of droplets;

c. measuring $\Delta X$ and determining $s = \lambda_1 d/X$; and d. determining $V_j$ by obtaining the product of *s* and *f*.

6. The method of claim 5 wherein the velocity $V_j$ for each of a plurality of streams is determined by scanning the coherent radiation.

* * * * *